United States Patent
Van Grinsven et al.

(10) Patent No.: US 10,139,407 B2
(45) Date of Patent: Nov. 27, 2018

(54) METHODS FOR DETECTING BACTERIA USING POLYMER MATERIALS

(71) Applicants: Universiteit Maastricht, Maastricht (NL); Academisch Ziekenhuis Maastricht, Maastricht (NL)

(72) Inventors: Bart Robert Nicolaas Van Grinsven, Heerlen (NL); Thomas Jan Cleij, Elsloo (NL)

(73) Assignees: Universiteit Maastricht, Maastricht (NL); Academisch Ziekenhuis Maastricht, Maastricht (NL)

( * ) Notice: Subject to any disclaimer, the term of this patent is extended or adjusted under 35 U.S.C. 154(b) by 0 days.

(21) Appl. No.: 15/095,636

(22) Filed: Apr. 11, 2016

(65) Prior Publication Data

US 2017/0292950 A1    Oct. 12, 2017

(51) Int. Cl.
*G01N 33/48* (2006.01)
*G01N 33/569* (2006.01)
*G01N 25/18* (2006.01)
*G01N 25/20* (2006.01)
*G01N 33/487* (2006.01)
*G01N 33/543* (2006.01)

(52) U.S. Cl.
CPC ....... *G01N 33/56911* (2013.01); *G01N 25/18* (2013.01); *G01N 25/20* (2013.01); *G01N 33/487* (2013.01); *G01N 33/54373* (2013.01); *G01N 2333/245* (2013.01); *G01N 2333/31* (2013.01)

(58) Field of Classification Search
None
See application file for complete search history.

(56) References Cited

U.S. PATENT DOCUMENTS

| 6,161,028 | A | 12/2000 | Braig et al. |
|---|---|---|---|
| 8,932,868 | B2 * | 1/2015 | Van Grinsven ...... C12Q 1/6825 422/50 |
| 9,228,970 | B2 * | 1/2016 | Van Grinsven ...... C12Q 1/6825 |
| 9,429,539 | B2 * | 8/2016 | Van Grinsven ...... C12Q 1/6825 |
| 9,435,798 | B2 * | 9/2016 | Eersels ................. G01N 25/18 |
| 2003/0059807 | A1 | 3/2003 | Roach et al. |
| 2003/0199742 | A1 | 10/2003 | Braig et al. |
| 2004/0034291 | A1 | 2/2004 | Braig et al. |
| 2004/0087841 | A1 | 6/2004 | Braig et al. |
| 2004/0126814 | A1 | 7/2004 | Singh et al. |
| 2006/0078999 | A1 | 4/2006 | Bell et al. |
| 2013/0327656 | A1 * | 12/2013 | Van Grinsven ...... C12Q 1/6825 205/780.5 |
| 2014/0011198 | A1 | 1/2014 | Van Grinsven et al. |
| 2014/0242605 | A1 * | 8/2014 | Eersels ................. G01N 25/18 435/7.1 |
| 2015/0219584 | A1 * | 8/2015 | Van Grinsven ...... C12Q 1/6825 204/403.01 |
| 2017/0292949 | A1 * | 10/2017 | Van Grinsven ............. G01N 33/54373 |
| 2017/0292950 | A1 * | 10/2017 | Van Grinsven ............. G01N 33/56911 |

FOREIGN PATENT DOCUMENTS

| EP | 2772753 A1 | 9/2014 | |
|---|---|---|---|
| JP | 2005345385 | 12/2005 | |
| WO | 0053086 | 9/2000 | |
| WO | 2004079001 A1 | 9/2004 | |
| WO | 2012076349 A1 | 6/2012 | |
| WO | WO-2017084885 A1 * | 5/2017 | ............ B01J 20/268 |

OTHER PUBLICATIONS

Peeters et al, Molecules, 2016, 21, 552, 14 pages; www.mdpi.com/journal/molecules.*
Van Grinsven et al., The Heat-Transfer Method: A Versatile Low-Cost, Label-Free, Fast and User-Friendly Readout Platform for Biosensor Applications, ACS Applied Materials and Interfaces, Aug. 8, 2014, pp. 13309-13318, vol. 6, No. 16.
European Search Report of copending EP application 15 19 4837 dated Feb. 22, 2016.

* cited by examiner

*Primary Examiner* — Nita M. Minnifield
(74) *Attorney, Agent, or Firm* — TraskBritt, P.C.

(57) ABSTRACT

A method for characterizing bacteria includes passing a liquid containing an analyte comprising a first bacteria and a second bacteria over and in contact with a polymer material on a substrate. The polymer material is formulated to bind to the first bacteria, and the first bacteria binds to the polymer material with a higher affinity than the second bacteria. A heat transfer property of the polymer material varies based on an amount of the analyte bound thereto. The method further includes binding a portion of the first bacteria and the second bacteria of the analyte to the polymer material, removing at least a portion of the second bacteria from the polymer material, detecting a temperature of the substrate, and calculating a concentration of the first bacteria in the liquid based at least in part on the temperature of the substrate.

20 Claims, 13 Drawing Sheets

METHODS FOR DETECTING BACTERIA USING POLYMER MATERIALS

TECHNICAL FIELD

Embodiments of the present disclosure relate generally to devices and methods of detecting bacteria using polymer materials.

BACKGROUND

Molecularly imprinted polymers (MIPs) can be used for detecting chemical substances in complex mixtures. In modern research, these polymers are of increasing interest for bioanalytical applications. Advantages of using these MIPs include easy and cheap production; mechanical, chemical, and thermal stability; reusability; and long shelf life. In recent years, the concept of molecular imprinting has been extended to surface imprinting of thin polymer films with micrometer-sized cells to create so-called "surface imprinted polymers" (SIPs) for the detection of proteins, glycoproteins, plant viruses, human viruses, bacteria, pollen, yeast cells, and even mammalian red blood cells. SIPs are polymeric materials with indentations at the surface, with a form and function matching part of a desired target. SIPs are suitable for bonding with larger objects (e.g., cells, bacteria, etc.), which do not diffuse quickly through pores of an MIP. Imprinting may occur after polymerization by softening the polymer. The detection of cells using biosensors described in literature is conventionally done by gravimetric detection, electronic read-out platforms or micro-fluidic techniques. However, these techniques are often time-consuming, provide difficulties for analysis, or require expensive equipment.

For example, temperature resistance of substrates having MIPs attached thereto based on the concentration of analytes is described in U.S. Patent Application Publication 2014/0011198 A1, "Heat-Transfer Resistance Based Analysis Bioparticles," published Jan. 9, 2014, the entire disclosure of which is hereby incorporated herein by reference.

A low-cost sensor platform providing the capability to differentiate between cells with slight differences in shape, size, and functionalities in functional groups on their surface would be a valuable tool for modern research and industry.

BRIEF SUMMARY

In some embodiments, a method for characterizing bacteria includes passing a liquid containing an analyte comprising a first bacteria and a second bacteria over and in contact with a polymer material on a substrate. The polymer material is formulated to bind to the first bacteria, and the first bacteria binds to the polymer material with a higher affinity than the second bacteria. A heat transfer property of the polymer material varies based on an amount of the analyte bound thereto. The method further includes binding a portion of the first bacteria and the second bacteria of the analyte to the polymer material, removing at least a portion of the second bacteria from the polymer material, detecting a temperature of the substrate, and calculating a concentration of the first bacteria in the liquid based at least in part on the temperature of the substrate.

In other embodiments, a method for characterizing a liquid comprising bacteria includes passing a liquid containing a first strain of bacteria and at least a second strain of bacteria over and in contact with a polymer material on a substrate. The polymer material is formulated to bind to the first strain of bacteria, and the first bacteria binds to the polymer material with a higher affinity than the at least a second bacteria. A heat transfer property of the polymer material varies based on an amount of material bound thereto. The method further includes binding a portion of the first bacteria and a portion of the at least a second bacteria to the polymer material, washing the polymer material to remove the at least a second bacteria therefrom, passing the liquid over the polymer material after washing the polymer material, washing the polymer material at least a second time to remove the at least a second bacteria therefrom, detecting a temperature of the substrate, and calculating a concentration of the first bacteria in the liquid based at least in part on the temperature of the polymer material.

DETAILED DESCRIPTION

The illustrations presented herein are not actual views of any particular device or method, but are merely idealized representations employed to describe example embodiments of the present disclosure. Elements common between figures may retain the same numerical designation.

As used herein, the terms "template molecule" and "template bacteria" respectively refer to molecules or bacteria used to form a molecularly imprinted polymer (MIP) or surface imprinted polymer (SIP). Such MIPs or SIPs can then detect "target molecules" or "binding partners," which have functionality corresponding to the template molecules used to form the MIP or SIP.

As used herein, the term "may" encompasses the word "can," and the term "may be" encompasses the words "is" or "are," depending on context. Furthermore, presence of the word "may" is intended to indicate options for practicing or implementing embodiments of the disclosure, without limitation.

Figure 1:
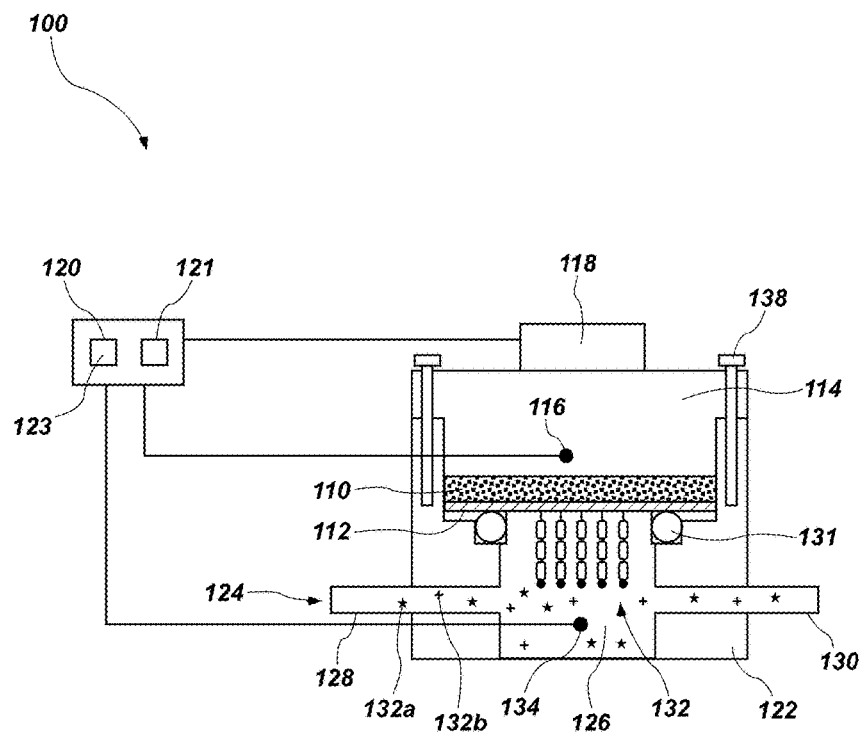
FIG. 1 is a simplified schematic diagram showing a device for detecting an analyte.

FIG. 1 is a simplified schematic diagram showing a device 100 for detecting an analyte. In some embodiments, the device 100 may be configured to detect bacteria.

The device 100 may include a substrate 110 having a polymer material 112 located over a surface thereof. For example, the polymer material 112 may be formed or disposed over a generally planar surface of the substrate 110, and another, opposite generally planar surface of the substrate 110 may be free of the polymer material 112. In some embodiments, the substrate 110 may include a metal (e.g., aluminum), an alloy, a semiconductor (e.g., silicon, doped diamond, etc.), an electrically insulating material (e.g., undoped diamond). The polymer material 112 may include any material for which a heat transfer property varies based on an amount of the analyte bound thereto. For example, the thermal conductivity, thermal diffusivity, heat capacity, or another property of the polymer material 112 may vary with concentration of the analyte on the surface thereof.

In some embodiments, the polymer material 112 may include an imprinted polymer, such as a molecularly imprinted polymer (MIP) or a surface imprinted polymer (SIP). MIPs and SIPs may also be referred to in the art as "plastic" antibodies. MIPs typically possess a high affinity for a specific binding partner, so that when such binding partners are contacted with the MIP, the molecules bind with the MIP. MIPs are synthetic receptors that contain nanocavities with high affinity for their respective target molecules. Imprinting (i.e., formation of the nanocavities) is often part of the polymerization process. MIPs are able to specifically bind targets, including bacteria, varying from small ions to large cells in complex matrices. Binding of molecules to the MIP may alter some properties of the MIP, such as thermal properties, mechanical properties, electrical properties, etc. The altered property of an MIP may, therefore, be used to detect a presence of such molecules at relatively low concentrations. MIPs are described in, for example, U.S. Patent Application Publication 2009/0281272 A1, "Monodisperse Molecularly Imprinted Polymer Beads," published Nov. 12, 2009, the entire disclosure of which is hereby incorporated herein by reference.

Similarly, SIPs typically possess a high affinity for a specific binding partner, but may typically bind to relatively larger objects (e.g., cells, bacteria, etc.) that do not diffuse quickly through pores of an MIP. SIPs may be polymer materials formed over a surface, then imprinted after polymerization by softening the polymer.

In certain embodiments, the polymer material 112 may include DNA, RNA, proteins, or portions or analogs thereof. For example, the device 100 may include a substrate 110 (e.g., a diamond surface) functionalized with a polymer material 112 such as DNA, RNA, a protein, a polypeptide, a nucleic acid polymer, a probe, or a portion or analog thereof (e.g., complementary DNA, antibodies, etc.). The polymer material 112 may be formulated to possess a high affinity for a specific binding partner, so that when such binding partners are contacted with the surface of the substrate 110, the molecules bind with the polymer material 112. The polymer material 112 may also bind to analogues of the binding partner (e.g., a material having similar functionality as the binding partner), though not necessarily with the same affinity as binding with the binding partner itself. In some embodiments, the polymer material 112 may include at least about seven (7) repeating units, such as ten (10) repeating units or more.

In some embodiments, the polymer material 112 may include a material screen-printed onto the substrate 110. Screen-printed materials may be manufactured efficiently and in mass quantities, with relatively high uniformity in comparison with other materials.

The device 100 may further include a heat sink 114 thermally coupled to a surface of the substrate 110, such as a surface opposite the polymer material 112. Though referred to as a heat "sink" for the sake of simplicity, the heat sink 114 may be configured to provide heat to or remove heat from the substrate 110 and, so, may also be characterized as a heat transfer element 114. The heat sink or heat transfer element 114 may be a material having a high thermal conductivity, such as a transition metal (e.g., copper, silver, etc.) or an alloy or mixture thereof. In some embodiments, the polymer material 112 may be applied to the heat sink 114 itself. The heat sink 114 may be thermally coupled to a temperature sensor 116 (e.g., a thermocouple or another device) configured to detect a temperature of the heat sink 114, and to a temperature modification device 118 configured to maintain the temperature of the heat sink 114. The temperature modification device 118 may include, for example, a thermoelectric device, a heat exchanger, a fan, a resistance heater, etc. The temperature sensor 116 may be a resistor having a resistance that varies with temperature. If the properties of the heat sink 114 are known (e.g., if a relationship between a control signal to the modification device 118 and the temperature of the heat sink 114 is well characterized), the temperature sensor 116 may be omitted. In some embodiments, the temperature sensor 116 may be integral to the temperature modification device 118. For example, the internal resistance of the temperature modification device 118 itself may be measured to determine its temperature.

The temperature sensor 116 and the temperature modification device 118 may be connected to a controller 121 configured (i.e., programmed) to control the temperature modification device 118 to cause the heat sink 114 to produce a thermal wave emanating from the heat sink 114 and through the substrate 110 (including the polymer material 112 thereon). For example, the controller 121 and a processor 123 may be incorporated into a computer 120 (e.g., the controller 121 may be an input-output card configured to receive and provide electrical signals, and may be configured to receive signals from the processor 123). In some embodiments, the controller 121 may be a proportional-integral-derivative (PID) controller capable of changing the temperature of the heat sink 114 by a small amount on a relatively short time scale. For example, the controller 121 may change the temperature of the heat sink 114 by about 0.5° C. or less, about 0.2° C. or less, or even about 0.05° C. or less. Thus, the thermal wave may have an amplitude of about 1.0° C. or less, about 0.4° C. or less, or even about 0.10° C. or less. The controller 121 may be capable of changing the temperature of the heat sink 114 via the temperature modification device 118 from one set point to another and back to form a thermal wave having a frequency from about 0.001 to about 0.5 Hz, such as from about 0.005 to about 0.1 Hz, or from about 0.01 to about 0.05 Hz. In some embodiments, the controller 121, the temperature modification device 118, and the heat sink 114 may together produce a thermal wave having a variable frequency. Based on a measurement from the temperature sensor 116 (if present), a known input to the temperature modification device 118, or other means, properties of the thermal wave may be known (e.g., a phase, amplitude, frequency at a specific time, rate of frequency change, etc.).

In other embodiments, the controller 121 may be configured to maintain the heat sink 114 at a constant temperature. Detection of analytes using a heat sink at constant temperature is described in U.S. Patent Application Publication 2015/0219584 A1, "Biosensor Using Impedimentric Real-Time Monitoring," published Aug. 6, 2015, the entire disclosure of which is hereby incorporated herein by reference.

The device 100 may further include a flow cell 122 configured to pass a liquid 124 over the polymer material 112 of the substrate 110. The flow cell 122 may define a void 126 adjacent the polymer material 112 of the substrate 110, as well as an inlet 128 and an outlet 130 through which the liquid 124 may flow. An O-ring 131 or another appropriate sealing mechanism may retain the liquid 124 within the flow cell 122 adjacent the polymer material 112 over the substrate 110.

The liquid 124 may include an analyte 132, such as one or more strains of bacteria. The analyte 132 (which may include multiple analytes 132a and 132b) may specifically bind to the polymer material 112 and changes thermal properties thereof, as described above. If multiple analytes 132a and 132b are present in the liquid 124, the analytes 132a, 132b may have similar functionalities, such that each of the analytes 132a, 132b bind to the polymer material 112. The analytes 132a, 132b may bind to the polymer material 112 with different affinities. In some embodiments, the first analyte 132a may include living bacteria, and the second analyte 132b may include dead bacteria of the same species. In other embodiments, the first analyte 132a may include bacteria, and the second analyte 132b may include an analogue bacteria.

A temperature sensor 134 (e.g., a thermocouple or another device) may be configured to detect a temperature of the liquid 124 in (e.g., flowing through) the flow cell 122. The computer 120 may record the temperature of the liquid 124 by, for example, measuring a resistance of the temperature sensor 134 via the controller 121 and/or the processor 123, and correlating that resistance to a temperature. The temperature of the liquid 124 may be different from the temperature of the heat sink 114, and may vary based at least in part on the presence or absence of the analyte 132 and its concentration in the liquid 124. For example, temperature resistance of substrates based on the concentration of analytes is described in U.S. Patent Application Publication 2014/0011198 A1, "Heat-Transfer Resistance Based Analysis Bioparticles," published Jan. 9, 2014, the entire disclosure of which is hereby incorporated herein by reference.

In some embodiments, the processor 123 may be configured to calculate a concentration of the analyte 132 in the liquid 124 based at least in part on a phase shift between the thermal wave produced by the heat sink 114 and an attenuated thermal wave in the liquid 124 after the thermal wave passes through the substrate 110 and the polymer material 112.

In other embodiments, the processor 123 may be configured to calculate a concentration of the analyte 132 based on a steady-state temperature difference between the heat sink 114 and the liquid 124.

Figure 2:
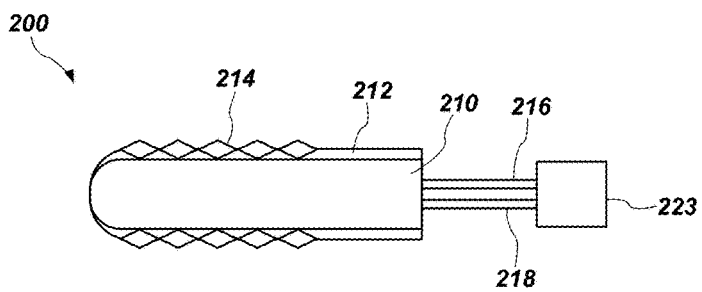
FIG. 2 is a simplified schematic diagram showing another device for detecting an analyte.

In certain embodiments, the analyte 132 may bind to a non-planar surface. For example, FIG. 2 is a simplified schematic diagram showing another device 200 for detecting the analyte 132. The device 200 may include a thermocouple 210 having a base material 212 formed over a surface thereof. For example, the base material 212 may be formed over a generally cylindrical surface of the thermocouple 210, such that an entire end of the thermocouple 210 is enclosed. The thermocouple 210 may include a junction between two materials formulated to provide a temperature-dependent voltage between electrical contacts 216, 218. In some embodiments, the thermocouple 210 may include one or more of a metal (e.g., platinum, gold, iridium, palladium, etc.) or an alloy (e.g., a nickel alloy, a copper alloy, a rhodium alloy, a rhenium alloy, an iron alloy, a molybdenum alloy, etc.).

The base material 212 may be a polymer material such as polylactic-(L)-acid, which may be referred to in the art as PLLA. PLLA is transparent, inexpensive to produce from environmentally renewable sources (e.g., starch or sugar-containing agricultural products), biodegradable, and biocompatible. Furthermore, PLLA can be solubilized in chloroform to enable application to the thermocouple 210. Another material, rather than PLLA, may be selected to be the base material 212, based on desired properties. In some embodiments, the base material 212 may include polyurethane, polylactic acid, polycaprolactone, poly(lactic-co-glycolic acid), poly(D,L-lactide-co-glycolide), or another selected polymer. The base material 212 may be in the form of a thin, smooth, and homogeneous coating over the exterior of the thermocouple 210. Uniformity of the coating by base material 212 may enable to the device 200 to yield reproducible results. The thickness of the base material 212 may be selected in view of the thermal resistance of the base material 212 to affect the rate at which heat may flow toward or away from the thermocouple 210. Thus, a thinner base material 212 may be beneficial for applications in which a fast response is desired or temperature differentials are small.

The base material 212 may be selected to exhibit at least some elasticity, such that the device 200 may be flexible to allow bending of the thermocouple 210 without breaking the base material 212. This may enable the device 200 to be used for applications requiring tight clearance or bends (e.g., in vivo use in catheters).

An assay polymer 214 may be on a surface of the base material 212. In some embodiments, the assay polymer 214 may be directly bonded to the surface of the thermocouple 210, and the base material 212 may be omitted. The assay polymer 214 may include a material for which a heat transfer property varies responsive to an amount of the analyte bound thereto. For example, the thermal conductivity, thermal diffusivity, heat capacity, or another property of the assay polymer 214 may vary with concentration of the analyte on the surface thereof.

In some embodiments, the assay polymer 214 may include an imprinted polymer (an MIP or SIP), DNA, RNA, proteins, or portions or analogs thereof (e.g., antibodies). The assay polymer 214 may be configured to possess a high affinity for a specific binding partner, so that when such binding partners are contacted with the surface of the thermocouple 210, the molecules bind with the assay polymer 214. In some embodiments, the assay polymer 214 may include at least about seven (7) repeating units, such as ten (10) repeating units or more.

In some embodiments, the device 200 may include a processor 223 programmed to calculate an amount of the analyte bound to the assay polymer 214. The processor 223 may calculate a concentration of the analyte in a liquid in contact with the device 200 based at least in part on the amount of the analyte bound to the assay polymer 214. For example, the processor 223 may calculate the amount of the analyte by a method as disclosed in U.S. Patent Application Publication 2014/0011198 A1, "Heat-Transfer Resistance Based Analysis Bioparticles," published Jan. 9, 2014; or U.S. Patent Application Publication 2014/0242605 A1, "Heat-Transfer Resistance Based Analysis of Bioparticles," published Aug. 28, 2014, the entire disclosures of each of which are hereby incorporated herein by reference. In certain embodiments, the processor 223 may be used to detect a phase shift between a thermal wave at or emanating from a heat sink and an attenuated thermal wave at the thermocouple 210. The processor 223 may then calculate the concentration of the analyte in the liquid based at least in part on a difference in amplitude between the thermal wave at the heat sink and the attenuated thermal wave at the thermocouple 210.

Returning again to FIG. 1, the polymer material 112 may be formed or otherwise provided over the substrate 110. For example, the polymer material 112 may be screen-printed onto a metal substrate 110. Screen-printing may be performed efficiently and scaled to produce mass quantities, with relatively high uniformity in comparison with other methods. Screen-printing of substrates is described in, for example, U.S. Patent Application Publication 2012/0186999 A1, "Electrochemical Sensor," published Jul. 26, 2012, the entire disclosure of which is hereby incorporated herein by reference.

The heat sink 114 may be thermally coupled to the substrate 110 at a surface opposite the polymer material 112. For example, the heat sink 114 may be placed in direct physical contact with the substrate 110 such that heat can flow from the heat sink 114 to the substrate 110 by conduction. In some embodiments, a thermally conductive material (e.g., a polymerizable liquid matrix having a thermally conductive filler) may be placed in physical contact with the heat sink 114 and the substrate 110 to eliminate air gaps between the heat sink 114 and the substrate 110. Similarly, the temperature modification device 118 may be thermally coupled to the heat sink 114 by direct physical contact, through a thermally conductive material, or by other appropriate means.

The flow cell 122 may be secured adjacent the substrate 110 such that the liquid 124 enters the flow cell 122 through the inlet 128, contacts the polymer material 112, and then leaves the flow cell 122 through the outlet 130. In some embodiments, the flow cell 122 may be connected to the heat sink 114 by one or more fasteners 138 (e.g., screws). In other embodiments, the flow cell 122 may be connected to the heat sink 114 by integral threads or by a slip-fit joint. The O-ring 131 or other seal may be configured to keep the liquid 124 from contacting the heat sink 114, the temperature modification device 118, or the back side of the substrate 110 directly.

The temperature sensor 134 may be disposed within the void 126 of the flow cell 122 to measure the temperature of the liquid 124 flowing through the flow cell 122. The temperature sensor 134 may be secured to the flow cell 122 by an adhesive or other appropriate means. The temperature sensor 134 may be electrically connected to the processor 123, which may include an ohmmeter. The processor 123 may be configured to continuously detect the temperature at the temperature sensor 134, and to calculate the concentration of the analyte 132 in the liquid 124.

The device 100 shown in FIG. 1 and described above may be used to detect any selected analyte 132, such as bacteria. For example, the device 100 may be used for detecting, sensing, and quantifying particular strains of bacteria, whether bacteria are living or dead, or discriminating types of bacteria in a complex mixture.

To detect the analyte 132, the liquid 124 containing the analyte 132 may be passed through the flow cell 122, adjacent and in contact with the polymer material 112 over the substrate 110. The analyte 132 (e.g., bacteria) binds to the polymer material 112, changing one or more thermal properties of the polymer material 112. The liquid 124 may flow continuously through the flow cell 122 during detection, or the flow may terminate before detection begins. In some embodiments, the flow cell 122 and the liquid 124 therein may be brought to a test temperature before detection of the analyte 132. As discussed above, the polymer material 112 may be a molecularly imprinted polymer formulated to bind a particular analyte 132 of interest.

In some embodiments, the first analyte 132a may be distinguished from the second analyte 132b by removing the second analyte 132b from the polymer material 112. For example, if the first analyte 132a is living bacteria, and the second analyte 132b is dead bacteria, the dead bacteria may be washed or rinsed from polymer material 112 (e.g., with a buffer), leaving the living bacteria behind. Differences in affinity between the first analyte 132a and the second analyte 132b may facilitate such discrimination. In some embodiments, the first analyte 132a may be the template molecule used to form the polymer material 112, and the second analyte 132b may be a molecule or bacteria having some similar functionality. Therefore the second analyte 132b may bind, at least weakly, to the polymer material 112.

EXAMPLES

Example 1: Bacterial Culturing and Sample Preparation

Characterized strains of *Escherichia coli* (ATCC® 8739™) and *Staphylococcus aureus* (ATCC® 6538™) were obtained from Leibniz Institute DSMZ, of Braunschweig, Germany. 20 ml of nutrient broth (item number x929.1, from Carl Roth GmbH+Co KG, of Karlsruhe, Germany) was inoculated with a single colony of *E. coli*. 20 ml of Caso broth (item number x938.1, from Carl Roth) was inoculated with a single colony of *S. aureus*. Both colonies were allowed to grow overnight at 37° C. while subject to agitation.

1 ml of each overnight culture was diluted in 20 ml of the respective broth, and allowed to grow at 37° C. for 3 hours or until $OD_{600}$ (i.e., optical density measured at a wavelength of 600 nm, a measurement correlated to concentration of the bacteria) of 1 was obtained. Afterwards, the cells were harvested by centrifuging to form pellets, which were washed one time with phosphate buffered saline (PBS), and then resuspended in PBS to achieve desired concentrations.

Example 2: Preparation of Bacteria-Imprinted Polyurethane Layers

A spin-coating solution was prepared by dissolving 122 mg of 4,4'-diisocyanatodiphenylmethane, 222 mg of bisphenol A, and 25 mg of phloroglucinol in 500 µL of anhydrous tetrahydrofuran (THF). All reagents had a purity of at least 99.9% and were used as received from Sigma-Aldrich N.V., of Diegem, Belgium. The solution was polymerized up to its gel point at 65° C. for 200 minutes while gently stirring. The solution was diluted in anhydrous THF in a 1:5 ratio. Polyurethane layers with an average thickness of 1.2±0.1 as measured with a profilometer (Dektak 3ST, Sloan Instruments Corporation, Santa Barbara, Calif., USA) were formed by spin-coating the solution for 60 s at 2000 rpm onto aluminum substrates each having a surface area of 1 cm$^2$.

Polydimethylsiloxane (PDMS) stamps were made using a Dow Corning SYLGARD® 184 silicone elastomer kit purchased from Malvom N.V., of Schelle, Belgium. Bacteria-covered PDMS stamps were formed by applying 400 µL of a bacteria suspension in PBS to each stamp. The bacteria were allowed to settle to the surface of the stamp for 60 s. The excess fluid was removed by spin-coating the stamps at 3000 rpm for 60 s to create a dense monolayer of bacteria on the stamp surface.

The bacteria-covered stamps were each pressed into the polyurethane layer on one of the aluminum substrates at a pressure of 70 Pa. The polyurethane was cured for 18 hours at 65° C. in an inert atmosphere, after which the stamps were removed from the surfaces of the substrates. Template bacteria were washed off with ethanol and PBS, leaving behind selective binding cavities on the surfaces of the substrates. Thus, surface-imprinted polymers (SIPs) were prepared to be selective for each of *E. coli* and *S. aureus*.

Example 3: Heat-Transfer Method (HTM)

A flow cell having an inside diameter of 6 mm and a height of 4 mm, with a total interior volume of 110 µl, was made of acrylic (available under the trademark PERSPEX®, from Lucite International, of Lancashire, United Kingdom). The flow cell was coupled to a potentiostat, and was sealed with an O-ring. The contact area between the flow cell and the potentiostat system was 28 mm$^2$. The SIP-coated substrates (described in Example 2) were mounted horizontally and pressed mechanically onto a copper block, which served as a heat sink. The temperature $T_1$ of the copper block was actively controlled by a proportional-integral-derivative (PID) controller with control parameters P=1, I=8, and D=0, and measured by a thermocouple. The temperature $T_1$ of the copper block was maintained at 37.00° C.

A second thermocouple was positioned above the surface of the SIP-coated substrates, which measured the temperature $T_2$ in the liquid. The thermal resistance, abbreviated as $R_{th}$ (° C./W), was determined by dividing the temperature difference $(T_1-T_2)$ by the input power P (in Watts) consumed while keeping the temperature constant at 37.00° C. (Equation 1).

$$R_{th} = \frac{T_1 - T_2}{P}. \qquad \text{Equation 1}$$

The SIP-coated substrates were stabilized in PBS buffer (pH=7.4) at the beginning of each experiment. Bacteria were introduced to the system by injecting 3 mL of a bacteria solution (1×10$^7$ CFU/mL in PBS) at a controlled flow rate of 2.5 mL/min. The SIP-coated substrates were stabilized, after which the SIP-coated substrates were flushed with PBS at a flow rate of 0.25 mL/min for 12 minutes (total volume 3 mL) to remove any unbound bacteria from the SIP layer. The HTM setup monitors the thermal resistance ($R_{th}$) at the solid-liquid interface at a rate of one measurement per second.

Example 4: Microscopic Imaging

Microscopic imaging of the SIP-coated substrates was performed with a DM750 optical microscope, available from Leica Microsystems, of Diegem, Belgium. The SIP-coated substrates were imaged at magnifications 640× and 1000×. Software (ImageJ version 1.44p, available from National Institutes of Health, Bethesda, Md., USA) was used to determine the number of cell imprints per unit area on microscopic images of the SIP-coated substrates. The average surface coverage of cell imprints was calculated based on cell imprint counts of three different samples for each type of SIP-coated substrate and at five locations on each SIP-coated substrate.

Figure 3:
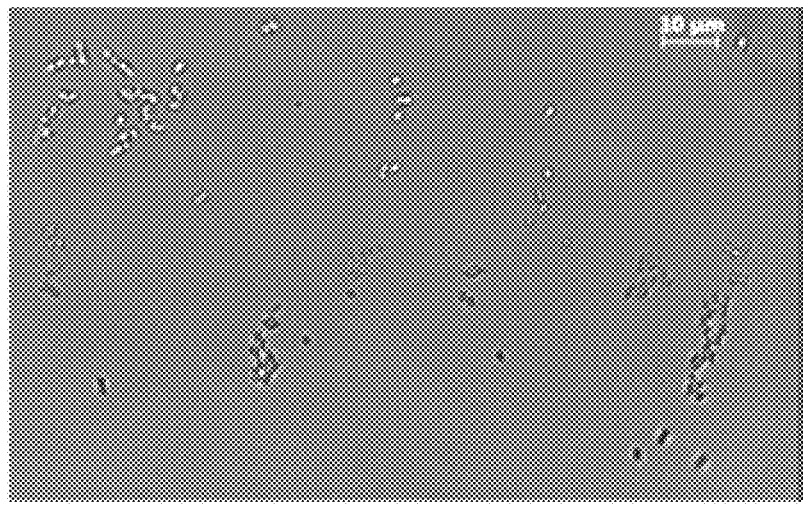
FIG. 3 is an optical microscopic analysis of a polymer imprinted with *E. coli;*
Figure 4:
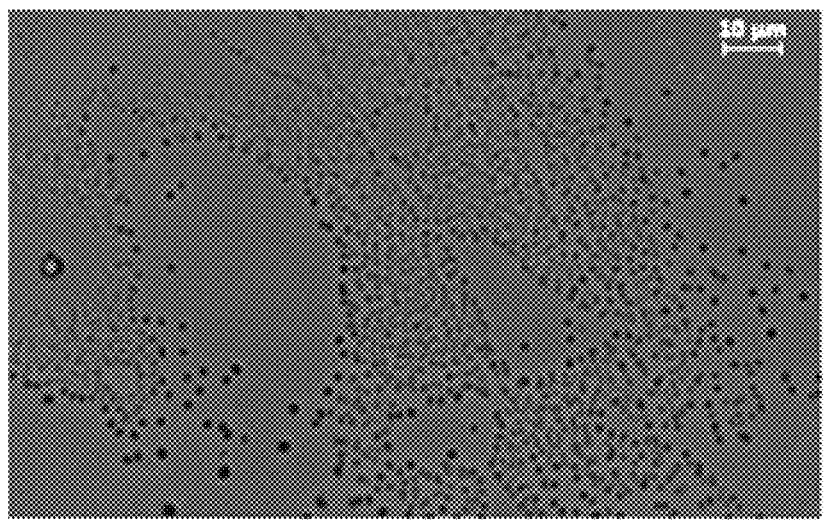
FIG. 4 is an optical microscopic analysis of a polymer imprinted with *S. aureus;*

Optical microscopic analysis of a SIP surface imprinted with *E. coli* (FIG. 3) clearly reveals rod-shaped imprints with a length varying from 1.5 to 3 µm and a width of 0.5 to 1.5 µm corresponding to the dimensions of the bacteria. A calculated surface coverage of 1.11×10$^6$±6.62×10$^5$ imprints/cm$^2$ corresponds to a total surface coverage of 6.02±1.6%. Optical microscopic analysis of an *S. aureus* SIP (FIG. 4) shows a heterogeneous distribution of spherical imprints with a diameter of ±500 nm-800 nm. The imprint surface coverage of 2.91×10$^6$±8.73×10$^5$ imprints/cm$^2$ corresponds to a total surface coverage of 9.12±2.1%.

Example 5: Discrimination Between Live and Dead Bacteria

A SIP-coated substrate was formed and imprinted with living $E.$ $coli$ cells in PBS (concentration $1\times10^7$ CFU/mL) as described in Examples 1 and 2. The SIP-coated substrate was mechanically pressed with its non-coated, polished backside onto a copper block, to ensure thermal contact between the SIP-coated substrate and the copper block. The SIP-coated substrate was placed in a flow cell, which was filled with PBS. The $R_{th}$ signal of the SIP-coated substrate was allowed to stabilize for 60 minutes. Dead bacteria were introduced into the flow cell for 72 s at a flow rate of 2.5 mL/min. The flow was stopped, and the $R_{th}$ signal was allowed to stabilize for 60 min, allowing the bacteria to sediment towards the SIP surface. Any unbound bacteria were removed by flushing the flow cell with PBS for 12 minutes at a rate of 0.25 mL/min. After a 60-minute stabilization interval, the experiment was repeated with living $E.$ $coli$ cells. The results of this experiment are shown in FIGS. 5 and 6.

Figure 5:
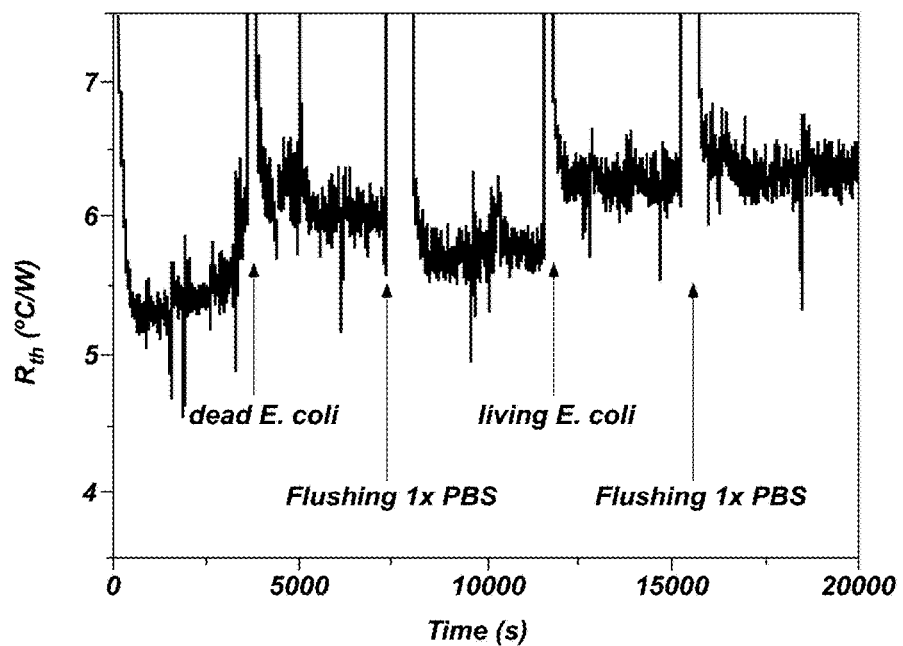
FIG. 5 is a graph showing thermal response of a device alternately exposed to dead and living *E. coli*, with flushing in between exposures.

FIG. 5 shows that both exposure events (i.e., exposure to living and dead $E.$ $coli$ cells) result in an increase in thermal resistance at the solid-liquid interface of the SIP-coated substrate. The increase associated with an addition of dead bacteria can be partially reversed by flushing with PBS, whereas the increase caused by adding living $E.$ $coli$ cells appears irreversible. FIG. 6 is a boxplot summarizing the data. Error bars indicate the standard deviation of the noise on the signal.

Figure 6:
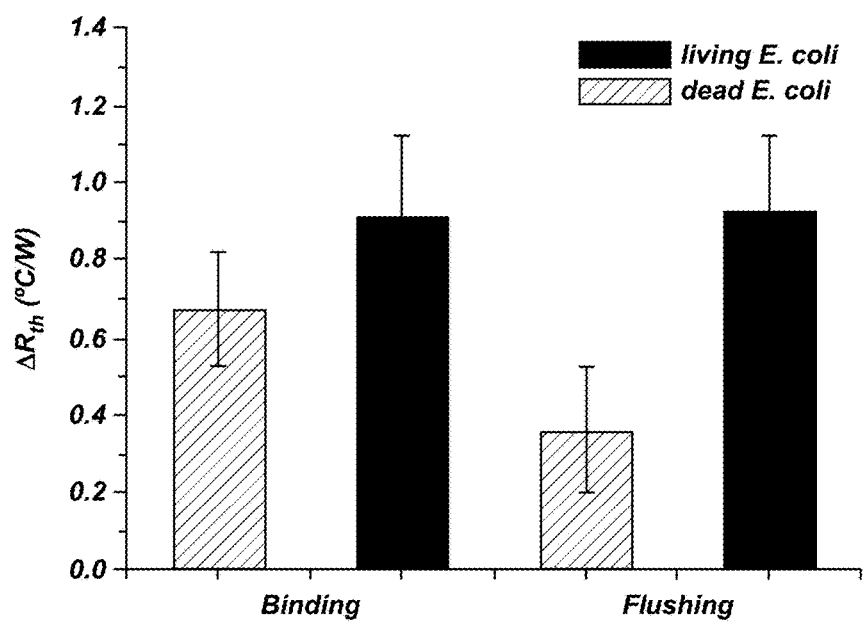
FIG. 6 is a boxplot summarizing the thermal responses shown in FIG. 5.

FIGS. 5 and 6 indicate that the signal ($R_d$) increases upon addition of a solution of dead bacteria in PBS by $0.67\pm0.15°$ C./W. Upon flushing the chamber with PBS the signal drops back to a value $0.36\pm0.16°$ C./W above the baseline. After infusing the live bacteria into the measuring chamber the signal increases again to a value $0.91\pm0.21°$ C./W. Flushing with buffer solution does not cause a measurable decrease in $R_{th}$, and the signal remains at $0.93\pm0.19°$ C./W above the baseline.

The thermal resistance tests described in Example 5 and in FIGS. 5 and 6 show comparable responses upon initial exposure to dead and living bacteria, although the increase in $R_{th}$ is somewhat lower for dead cells. The morphology of the dead bacteria cells appears to be compatible with the dimensions of microcavities on the imprinted polymer surface. Additionally, dead bacteria express some bacteria-specific functional groups on their outer membranes, which may provide a partial functional match between the dead bacteria and the imprinted surface. Both living and dead cells alter heat flow properties through microcavities of the polymer, typically increasing thermal resistance at the solid-liquid interface. Rinsing the imprinted surface may provide sufficient shear forces to remove the dead bacteria from microcavities on the imprinted surface. Exposure of the imprinted surface to living $E.$ $coli$, on the other hand, may produce an increase in thermal resistance that cannot be reversed by a simple flushing. The bond between the imprints and living bacteria appears to be more stable than the bond between imprints and dead bacteria. Differentiation between dead and living bacteria from the same species may be based on chemical functionalization created within microcavities during imprinting.

Example 6: Selectivity Between $E.$ $coli$ and $S.$ $aureus$

SIP-coated substrates were formed and imprinted with $S.$ $aureus$ cells (gram-positive bacteria) and $E.$ $coli$ cells (gram-negative bacteria) as described in Examples 1 and 2. The SIP-coated substrates were mechanically pressed with their non-coated, polished backsides onto copper blocks, to ensure thermal contact between the SIP-coated substrates and the copper blocks. The SIP-coated substrates were placed in a flow cell, which was filled with PBS. Time-dependent $R_{th}$ data were acquired by consecutively exposing the SIP-coated substrates to analogue non-target bacteria and target bacteria. The flow cell was flushed at a controlled velocity between both exposure events.

Figure 7:
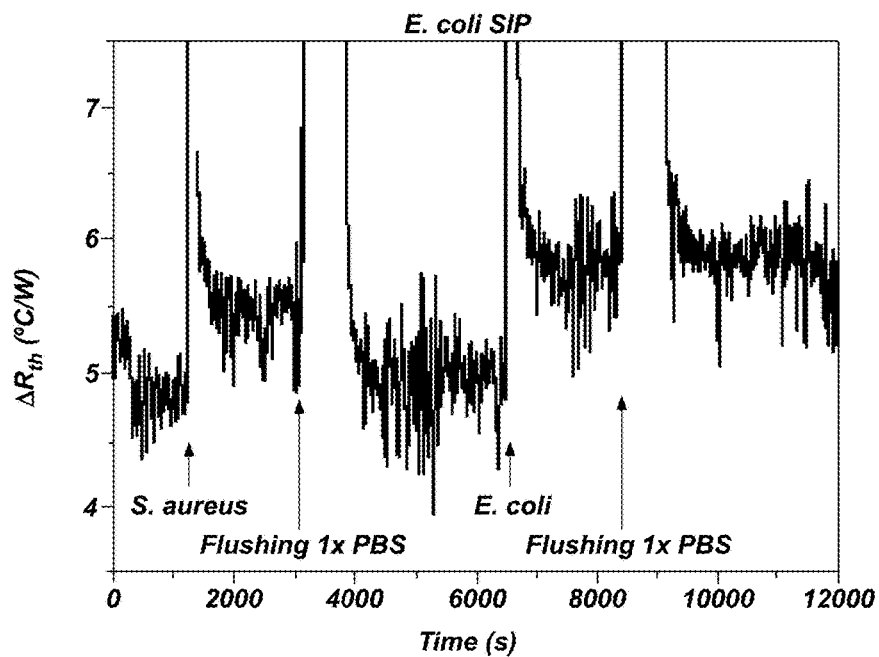
FIG. 7 is a graph showing thermal responses of a device alternately exposed to *S. aureus* and *E. coli*, with flushing in between exposures.
Figure 8:
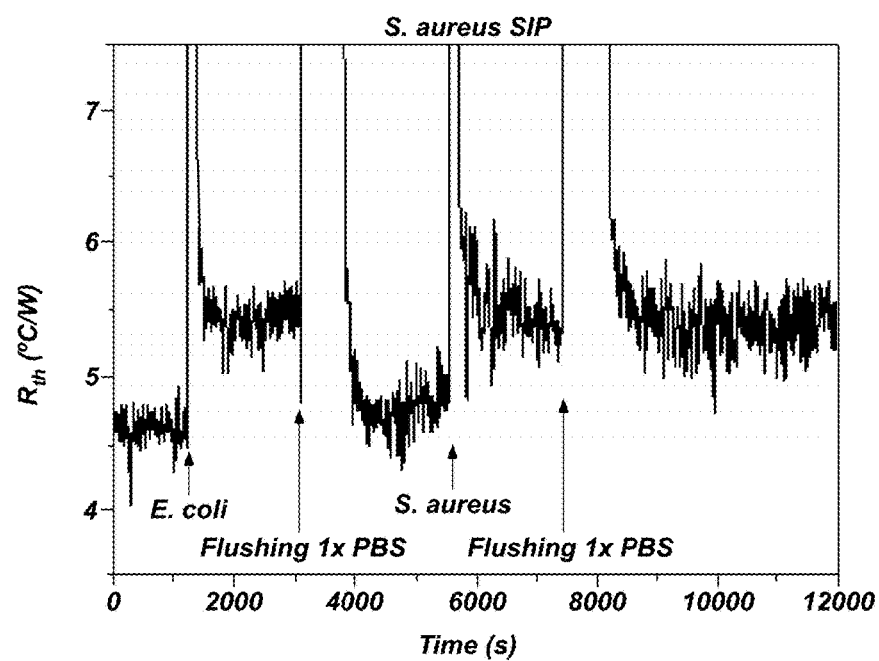
FIG. 8 is a graph showing thermal responses of a device alternately exposed to *E. coli* and *S. aureus*, with flushing in between exposures.

FIG. 7 shows that exposing an $E.$ $coli$-imprinted SIP to a suspension of $S.$ $aureus$ cells in PBS (concentration $1\times10^7$ CFU/mL) increased the thermal resistance at the solid-liquid interface with by $0.62\pm0.14°$ C./W. Rinsing the flow cell with PBS returned the signal back to baseline ($\Delta R_{th}=0.07\pm0.21°$ C./W). Repeating the cycle with an $E.$ $coli$ solution having the same concentration produced an irreversible increase in $R_{th}$ of $0.96\pm0.16°$ C./W ($\Delta R_{th}$ upon flushing=$0.94\pm0.12°$ C./W). A similar trend was observed when exposing an $S.$ $aureus$-imprinted SIP to $E.$ $coli$ followed by $S.$ $aureus$, as shown in FIG. 8. Exposure to a solution of $E.$ $coli$ cells increased the $R_{th}$ signal with $0.76\pm0.09°$ C./W but upon rinsing the flow cell with PBS, the thermal resistance stabilized at a value $0.12\pm0.11°$ C./W above the baseline. Exposing the SIP to a solution of target cells, led to an increase in thermal resistance of $0.91\pm0.17°$ C./W. Flushing the cell with PBS did not significantly change the signal ($0.87\pm0.19°$ C./W).

Figure 9:
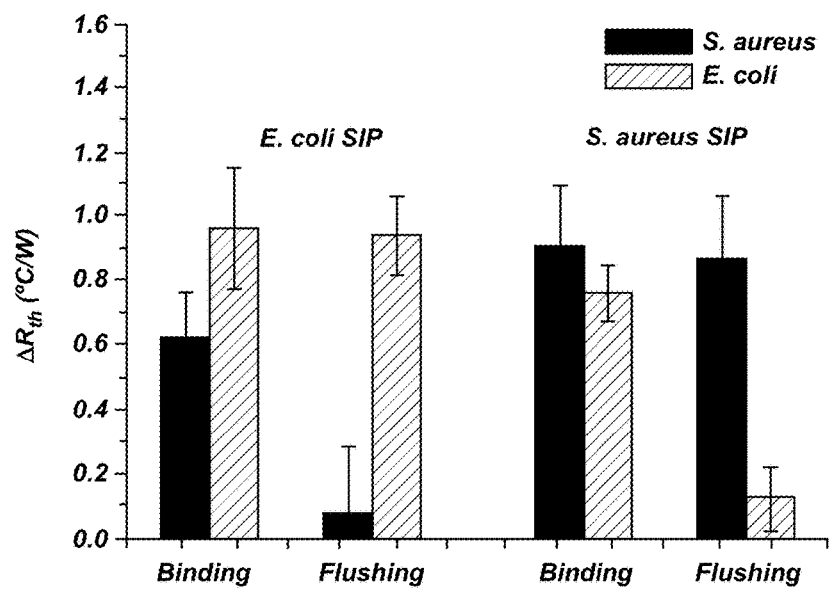
FIG. 9 is a boxplot summarizing the thermal responses shown in FIGS. 7 and 8.

Thus, FIGS. 7 and 8 each shown time-dependent $R_{th}$ measurements of SIPs imprinted with either $E.$ $coli$ (FIG. 7) or $S.$ $aureus$ (FIG. 8) during consecutive bacterial exposure events to analogue non-target bacteria and finally to target bacteria. In both cases, addition of non-target bacteria species led to an increase in thermal resistance, but the signal returned to near baseline upon flushing the flow cell with buffer solution. Binding of target bacteria to the SIP led to an irreversible rise in $R_{th}$. The results of these experiments are summarized in a box plot in FIG. 9.

Example 7: Sensitivity Test and Dose-Response Curve

Figure 10:
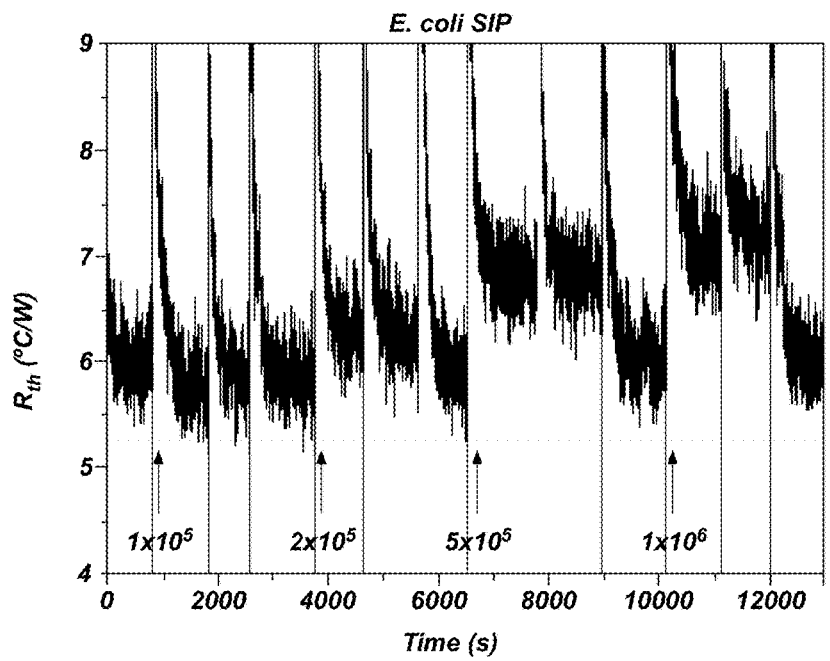
FIG. 10 is a graph showing thermal response of a device exposed to increasing concentrations of *E. coli*, with flushing in between exposures.

Portions of a stock solution of $E.$ $coli$ cells in PBS with a concentration of $1\times10^7$ CFU/mL were diluted 100, 50, 20 and 10 times, and a SIP-coated substrate (imprinted with $E.$ $coli$, as described in Examples 1 and 2) was consecutively exposed to an increasing concentration of target $E.$ $coli$ cells in a flow cell. In between each exposure step, the flow cell was rinsed with ethanol for 12 minutes at a rate of 0.25 mL/min, followed by a rinse with PBS for 12 minutes at a rate of 0.25 mL/min. The results of this experiment are shown in FIG. 10. The results identify the limit-of-detection (LoD) of the SIP-coated substrate.

Figure 11:
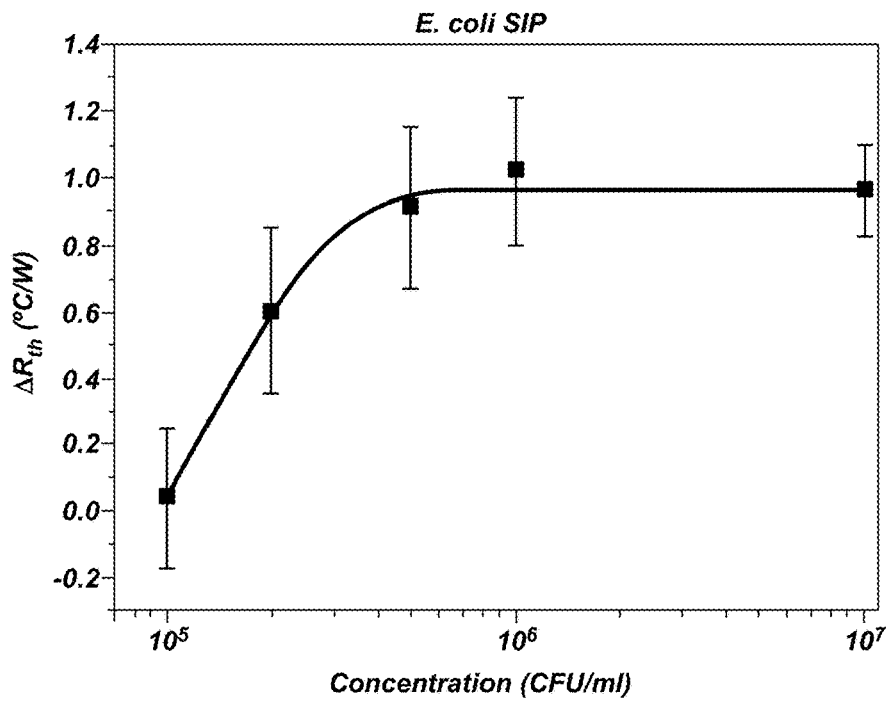
FIG. 11 is a dose-response curve derived from the thermal responses shown in FIG. 10.

The thermal resistance increased when the $E.$ $coli$ cells were added, and the increases appear to be concentration-dependent. The time-dependent thermal resistance data shown in FIG. 10 indicate that exposing the SIP-coated substrate to a concentration of $1\times10^5$ CFU/mL did not result in a measurable increase in $R_{th}$. Upon addition of a concentration of $2\times10^5$ CFU/mL, the signal started to increase. The signal appeared to start saturating at a concentration of $5\times10^5$ CFU/mL. These results combined with the results from the previous experiment were used to establish a dose-response curve shown in FIG. 11 showing a response in $R_{th}$ as a function of the added target-bacteria concentration on a logarithmic scale.

The dose-response curve follows an empirical, exponential fit function according to the formula:

$$\Delta R_{th}(c) = A - B \times \exp\left\{-\frac{c}{C}\right\},$$

where c is the concentration of *E. coli*, and A, B, and C are constants. The exponential fit drawn through the obtained data in FIG. 11 has an $R^2$-value of 0.9901.

The sensitivity tests described in Example 7 and FIGS. 10 and 11 reveal that sensors as described herein qualitatively respond to an elevated concentration of target bacteria species in a sample and that the response can be quantified. At relatively low concentrations, the sensor's response may remain within noise levels. But starting from a threshold concentration (about $2 \times 10^5$ CFU/mL in Example 7), the $R_{th}$ signal increases to a value high enough above the baseline to be statistically distinguishable (indicating that a sufficient amount of cells interacts with and binds to the microcavities on the imprinted polymer, blocking heat flow through the polymer and thereby increasing the heat-transfer resistance). This effect becomes more pronounced with an increasing concentration, but the polymer seems to saturate (at concentrations above $5 \times 10^5$ CFU/mL in Example 7). Using the exponential fit to the data and defining the detection limit as the concentration at which the signal-to-noise ratio is larger than 3, the limit of detection (LoD) for the sample in Example 7 was $1.5 \times 10^5$ CFU/mL. The LoD may be affected by, for example, the synthesis protocol for bacterial imprinting, including sedimentation time, spin-coat velocity and acceleration, template concentration, and surface functionalization of the stamp surface. In addition, the noise of the signal may be improved by electronic noise reduction, shielding, insulation, etc.

Example 8: Detection of *E. coli* in a Semi-Complex Matrix

A solution was prepared containing both *E. coli* and *S. aureus* cells in a 1:99 ratio. The total concentration of bacteria was $1 \times 10^7$ CFU/mL. This mixture was used in a progressive enrichment experiment.

Figure 12:
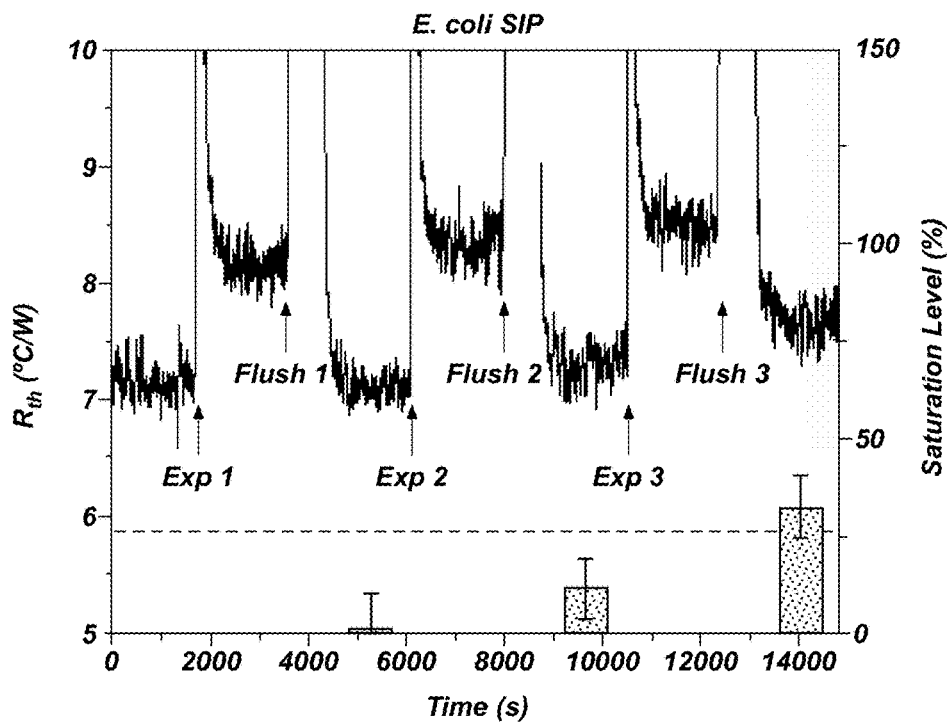
FIG. 12 is a graph showing thermal responses of a device exposed to a mixture of *E. coli* and *S. aureus*, with flushing in between exposures, as well as a boxplot summarizing the thermal responses.
Figure 13:
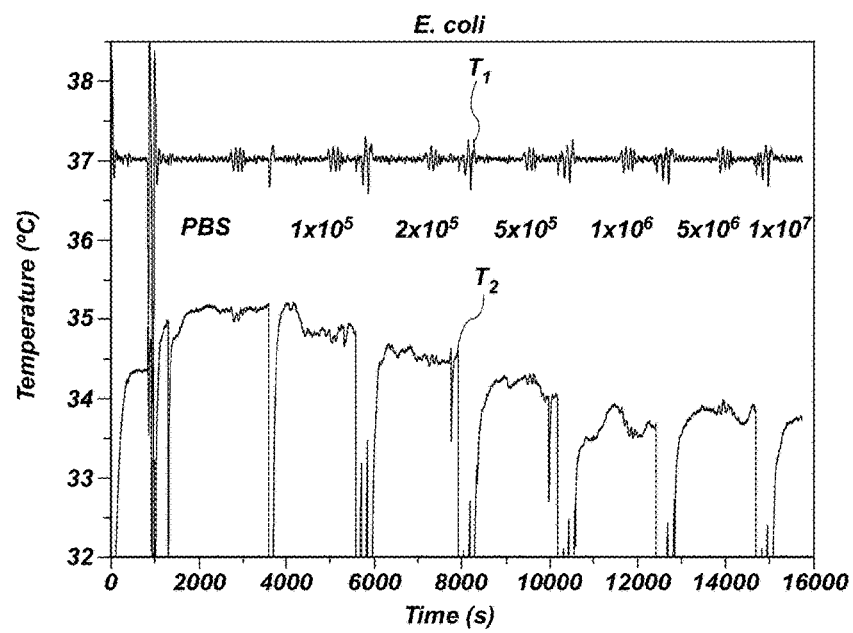
FIG. 13 is a graph showing changes in temperature of a device having a bacteria-imprinted polyurethane layer selective to *E. coli;*
Figure 14:
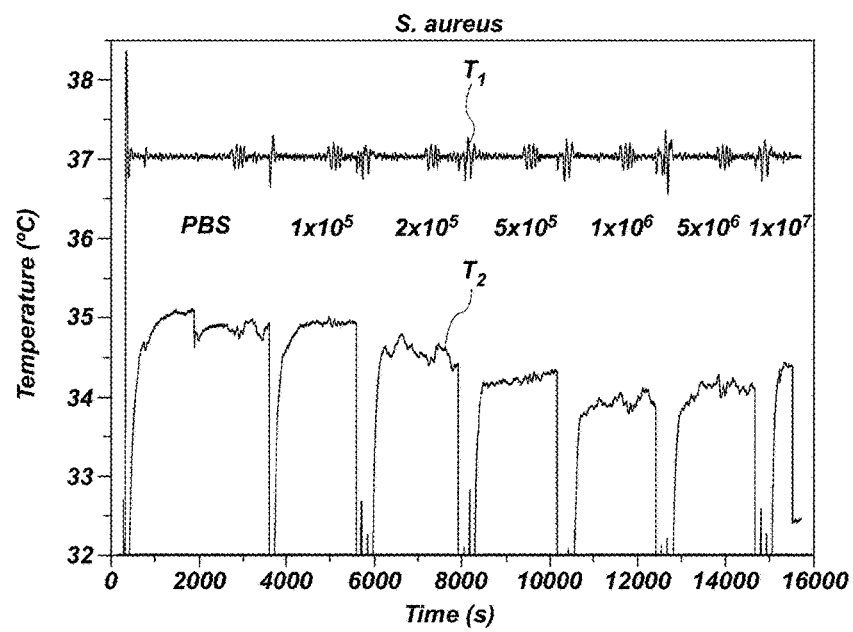
FIG. 14 is a graph showing changes in temperature of a device having a bacteria-imprinted polyurethane layer selective to *S. aureus;*
Figure 15:
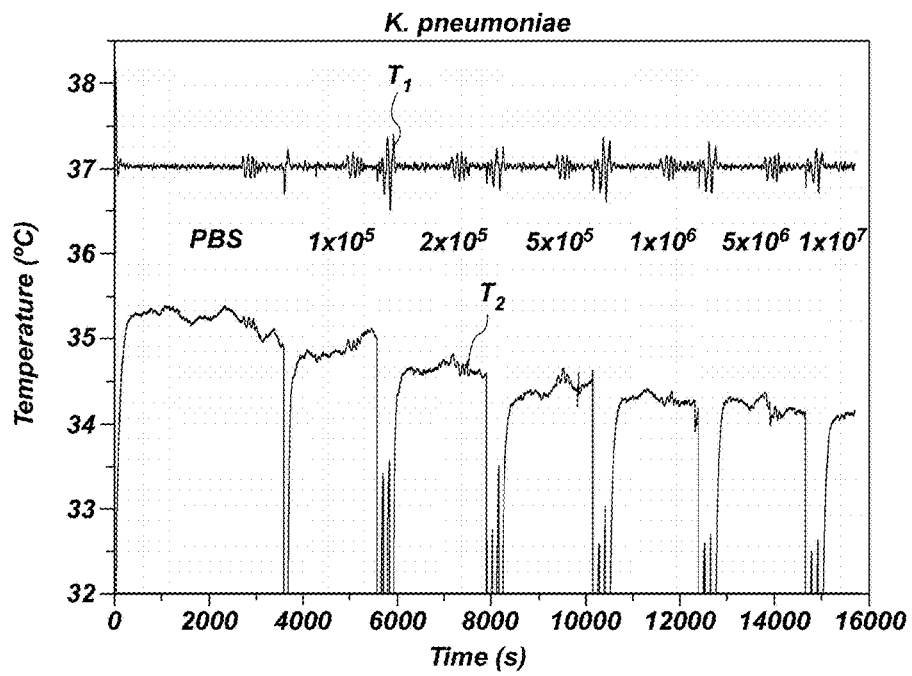
FIG. 15 is a graph showing changes in temperature of a device having a bacteria-imprinted polyurethane layer selective to *K. pneumoniae;*
Figure 16:
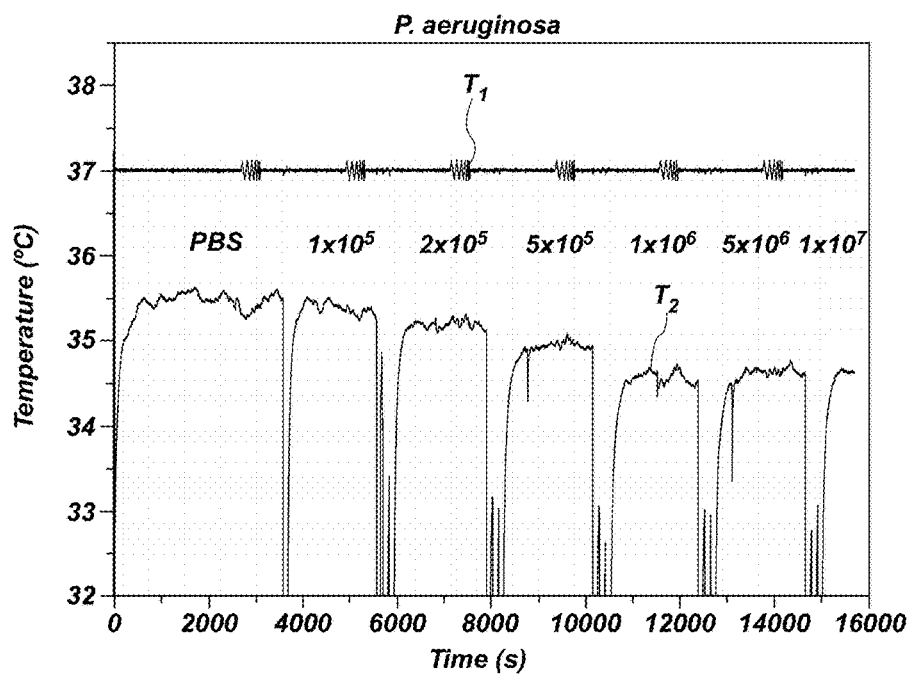
FIG. 16 is a graph showing changes in temperature of a device having a bacteria-imprinted polyurethane layer selective to *P. aeruginosa;*
Figure 17:
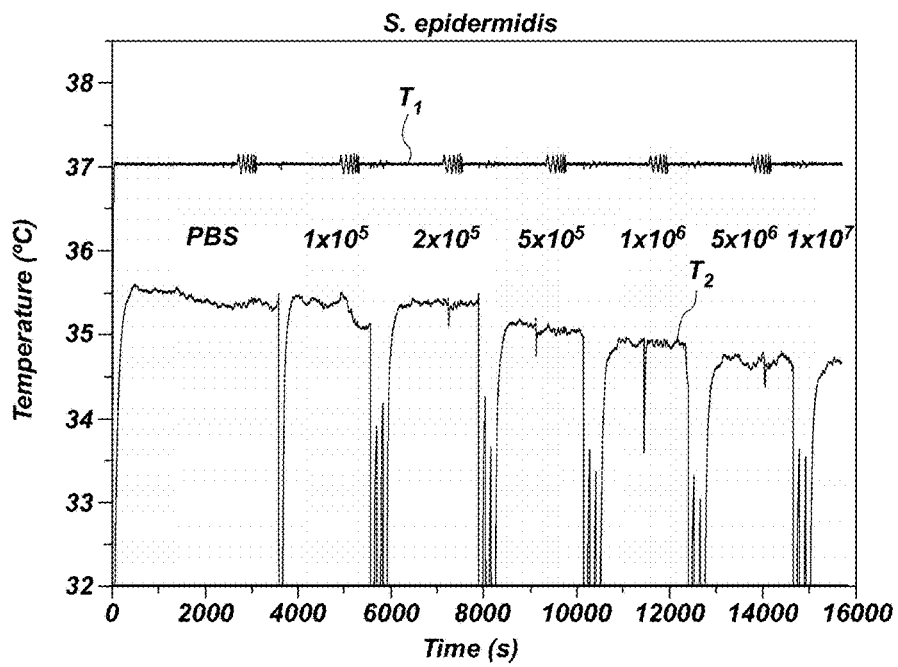
FIG. 17 is a graph showing changes in temperature of a device having a bacteria-imprinted polyurethane layer selective to *S. epidermidis;*
Figure 18:
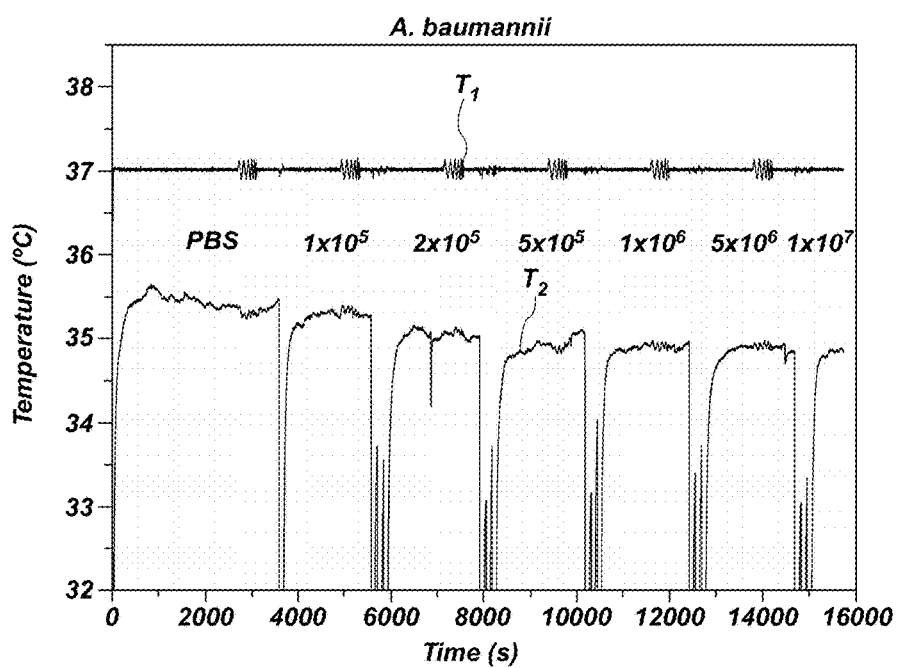
FIG. 18 is a graph showing changes in temperature of a device having a bacteria-imprinted polyurethane layer selective to *A. baumannii;*
Figure 19:
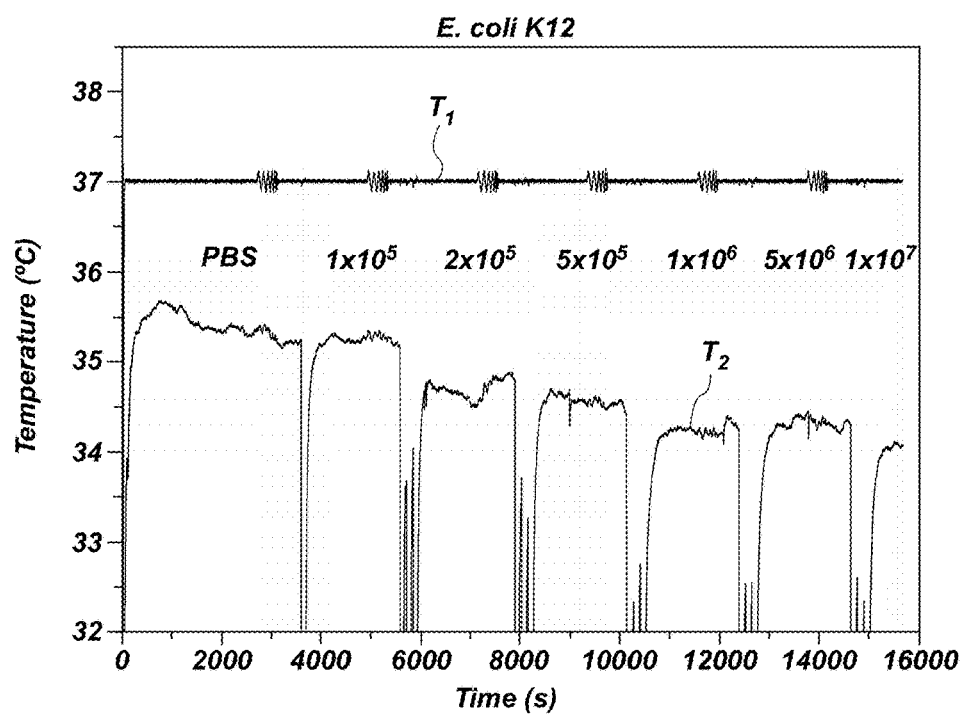
FIG. 19 is a graph showing changes in temperature of a device having a bacteria-imprinted polyurethane layer selective to *E. coli* K-12.
Figure 20:
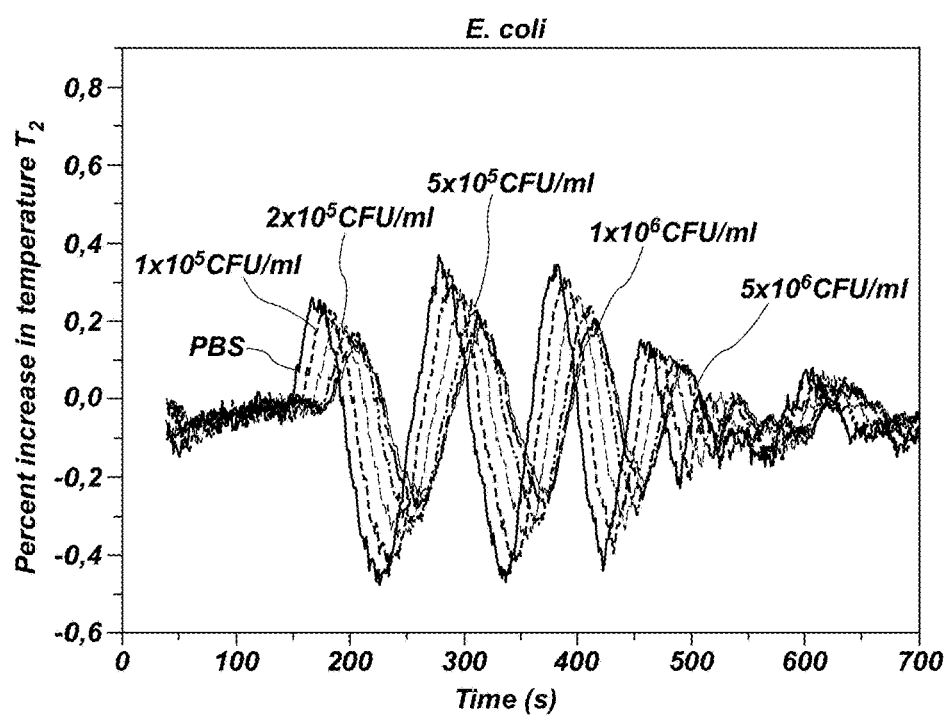
FIG. 20 is a graph showing thermal waves measured after passing through the device having a bacteria-imprinted polyurethane layer selective to *E. coli*, for which the temperature changes are shown in FIG. 13.
Figure 21:
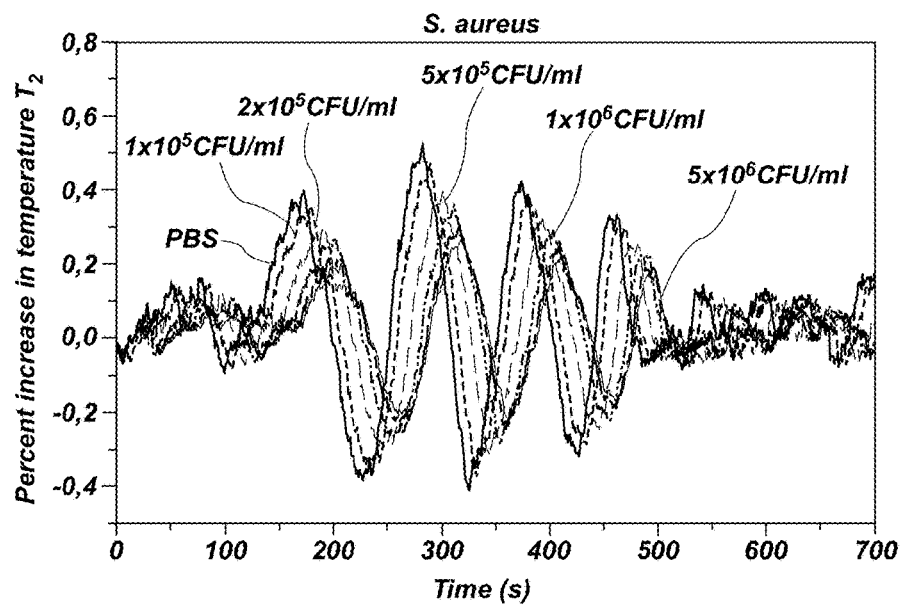
FIG. 21 is a graph showing thermal waves measured after passing through the device having a bacteria-imprinted polyurethane layer selective to *S. aureus*, for which the temperature changes are shown in FIG. 14.
Figure 22:
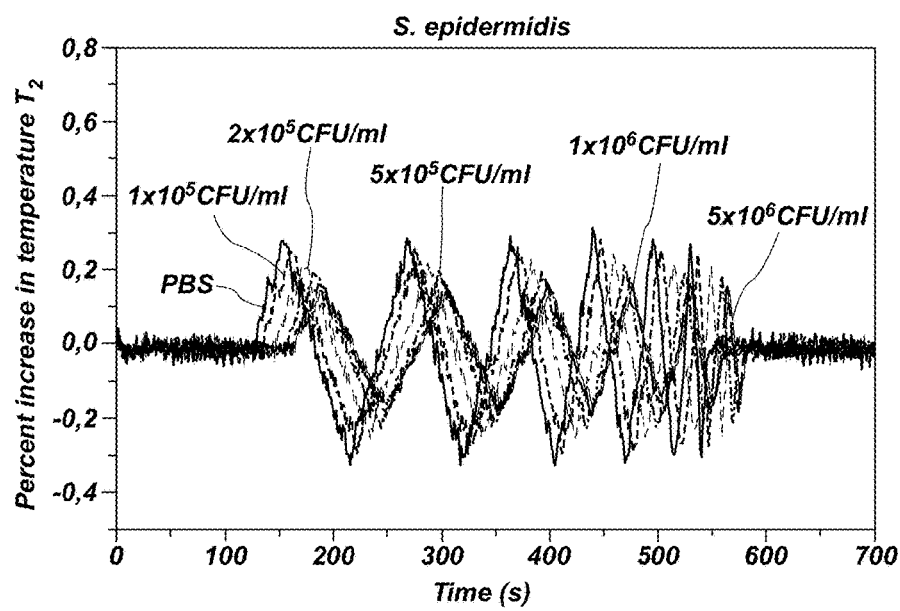
FIG. 22 is a graph showing thermal waves measured after passing through the device having a bacteria-imprinted polyurethane layer selective to *K. pneumoniae*, for which the temperature changes are shown in FIG. 15.
Figure 23:
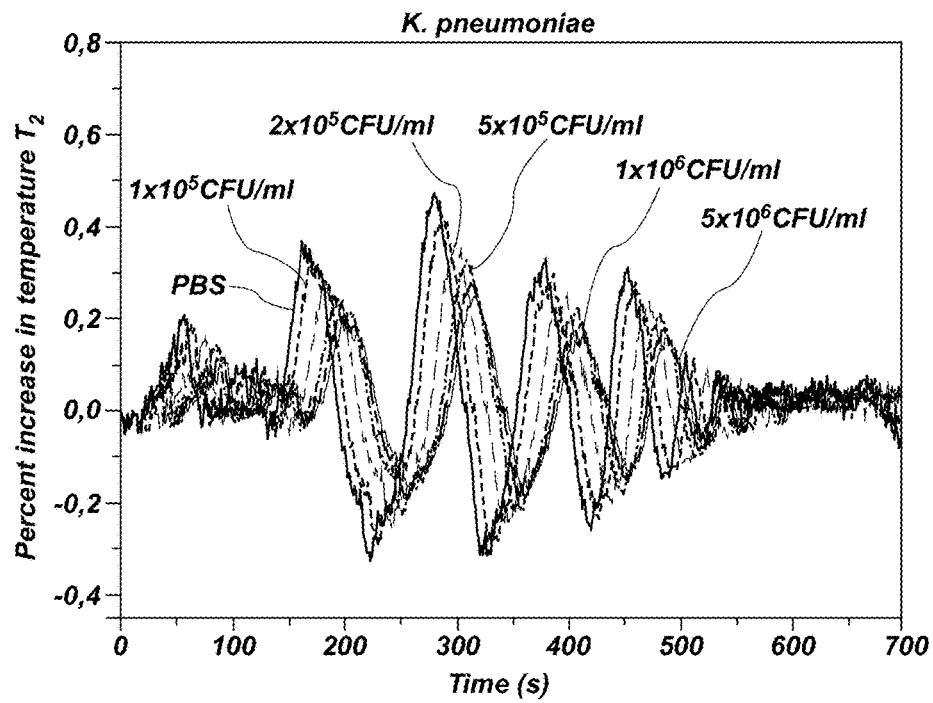
FIG. 23 is a graph showing thermal waves measured after passing through the device having a bacteria-imprinted polyurethane layer selective to *P. aeruginosa*, for which the temperature changes are shown in FIG. 16.
Figure 24:
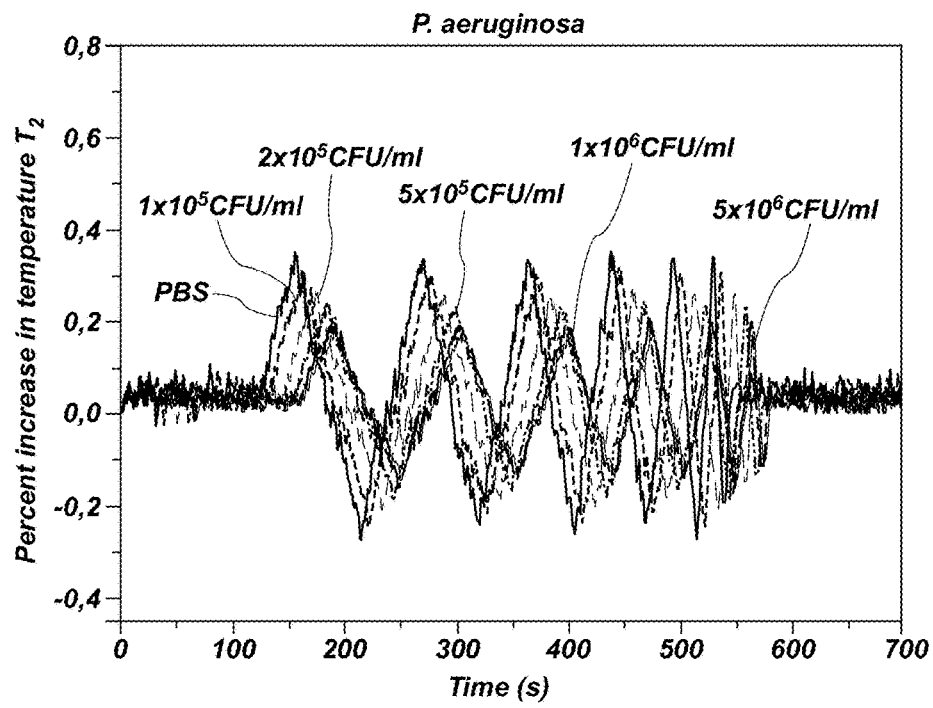
FIG. 24 is a graph showing thermal waves measured after passing through the device having a bacteria-imprinted polyurethane layer selective to *S. epidermidis*, for which the temperature changes are shown in FIG. 17.
Figure 25:
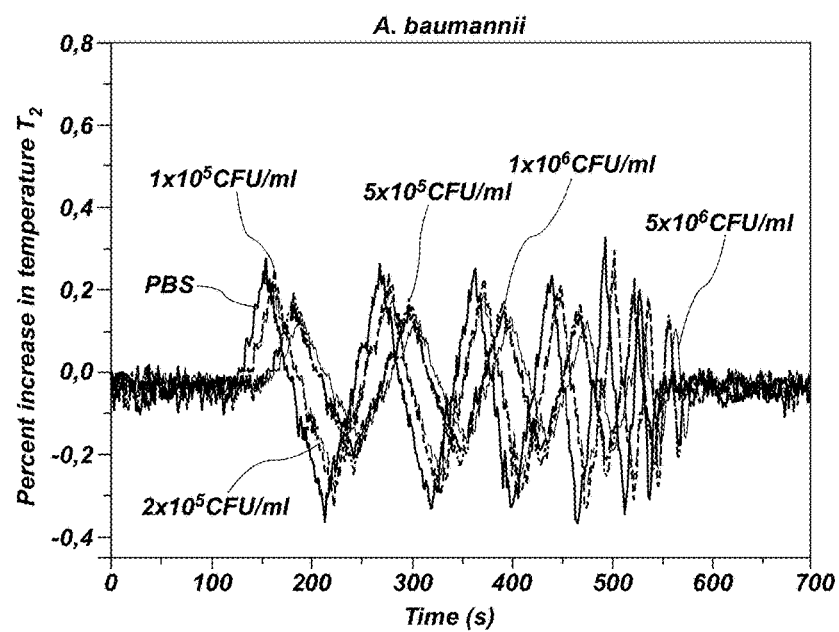
FIG. 25 is a graph showing thermal waves measured after passing through the device having a bacteria-imprinted polyurethane layer selective to *A. baumannii*, for which the temperature changes are shown in FIG. 18.
Figure 26:
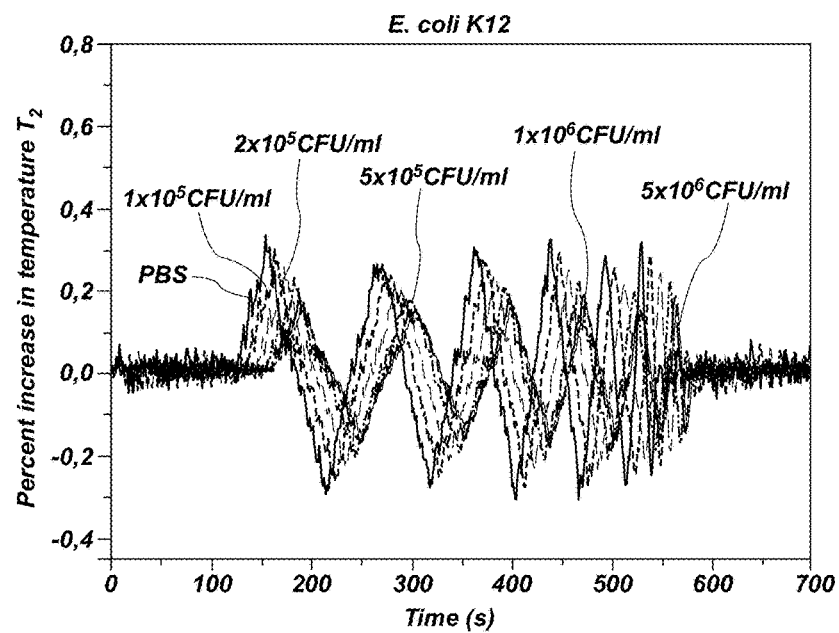
FIG. 26 is a graph showing thermal waves measured after passing through the device having a bacteria-imprinted polyurethane layer selective to *E. coli* K-12, for which the temperature changes are shown in FIG. 19.

A SIP-coated substrate was imprinted with *E. coli*, as described in Example 2. The substrate was exposed three consecutive times to the mixture, and the substrate was flushed with buffer between each exposure event. The results are shown in FIG. 12, and indicate that the signal ($R_{th}$) does not significantly increase in comparison to the baseline after the first exposure event. $R_{th}$ increases after the second and third exposure steps. After exposure to the bacteria mixture, the $R_{th}$ signal initially increased to saturation.

The saturation level at each step (indicated using the scale on the right of FIG. 12) was determined as the ratio of $\Delta R_{th}$ after exposure to the mixture and after flushing with buffer respectively. The LoD is illustrated as a dashed line and is defined as three times the standard deviation on the signal, corresponding to 26.4%. After the first two cycles, the signal only reaches 0.8±8.1% and 11.8±7.8%, well below the detection limit. After a third exposure round, the signal exceeds the limit of detection at a saturation level of 32.1±8.0%

Without being bound to any particular theory, it appears that both target and analogue cells bound to the SIP-coated substrate in the first exposure. After flushing, the signal fell back to a value that did not significantly differ from the baseline value. The total concentration of target cells (*E. coli*) in the mixture was only $1 \times 10^5$ CFU/mL, which is below the LoD determined in Example 7. Moreover, the *E. coli* cells were outnumbered 99:1 by *S. aureus* cells, an analogue bacteria that also bind to the microcavities in the SIP-coated substrate. *E. coli* cells cannot bind to microcavities that are already occupied by *S. aureus* cells. The analogue bacteria may also prevent the target bacteria from interacting with the SIP-coated substrate, due to steric hindrance.

These problems may be at least partially overcome by increasing the number of exposure cycles. With each cycle, the signal appeared to saturate and eventually reach the LoD, indicating that enrichment may improve the sensitivity of the SIP-coated substrate and may enable it to detect lower concentrations of bacteria in increasingly complex mixtures.

Example 9: Thermal Wave Analysis to Detect Bacterial Species

Seven bacteria-imprinted polyurethane layers selective to *E. coli*, *S. aureus*, *K pneumoniae*, *P. aeruginosa*, *S. epidermidis*, *A. baumannii*, and *E. coli* K-12 were formed as described in Example 2. The polyurethane layers were placed on aluminum substrates in flow cells as described in Example 3. The flow cells were each configured to vary the temperature $T_1$ of the copper block a function of time.

Each substrate was subjected to increasing concentrations of target bacteria in buffer solution. For each concentration of target bacteria, the temperature $T_1$ was kept constant for a period of time, then varied to apply a thermal wave. The temperature under the substrate was kept constant at 37° C. by applying power P. The temperature $T_2$ of the liquid flow cell was monitored in time. The thermal resistance (i.e., $R_{th}=(T_1-T_2)/P$) was also monitored over time. The results are shown in FIGS. 13 through 19.

These results show that the temperature ($T_2$) in the liquid flow cell decreases when the amount of target bacteria in the flow cell increases. This appears to indicate that bacteria are binding to the polyurethane on the substrate, increasing the thermal resistance ($R_{th}$) at the solid-liquid interface, which in turn causes $T_2$ to drop.

The thermal waves at each concentration were analyzed, and are shown in FIGS. 20 through 26. The relative change in $T_2$ was determined for each wave and the results were plotted in time, relative to the input wave.

The data in FIGS. 20 through 26 show that increasing the concentration of target bacteria in the flow cell leads to a phase shift in the thermal wave transmitted through the substrate and a decrease in amplitude of the thermal wave. Without being bound to any particular theory, it appears that as bacteria bind to the polyurethane over the substrate, the thermal resistance at the interface increases, inhibiting thermal energy to transfer to the liquid. This can be seen from the amplitude change of the wave. Additionally, the thermal wave dissipates slower over the chip resulting in the observed phase shift. The phase shift and/or amplitude change can be linked to the concentration of bacteria in the sample, and may be used to characterize the sample.

It has been unexpectedly discovered that the methods and devices described herein may be used to discriminate not only between strains of similar bacteria, but also between living and dead bacteria of the same strain. Without being bound to any particular theory, it appears that the difference in surface chemistry between living and dead *E. coli* is sufficient to discriminate between them, despite their morphological similarities.

Furthermore, it has been unexpectedly discovered that rinsing non-target analytes (e.g., bacteria similar but not identical to a target analyte bacteria) can increase the detection capability of a polymer material by freeing binding sites of non-target analytes without removing target analytes from other binding sites. Thus, binding sites that were initially occupied by target analytes may remain filled, and binding sites that were initially occupied by non-target (but analogue) analytes may be cleared for re-binding with another analyte (in particular, with the target analyte). Analogue bacteria may bind to imprints to some extent, possibly due to the presence of bacteria-specific functional groups on the membrane of the cells that are compatible to some of the functional groups inside the imprints. However, the bond does not appear to withstand shear forces provided by flushing. The target bacteria, on the other hand, appear to remain firmly bound to the polymer, such that the thermal resistance remains at an elevated level even after flushing. Such clearing and re-binding may be useful for characterizing complex mixtures of similar or related analytes because related analytes may tend to weakly bind to sites imprinted for one another. By clearing and re-binding analytes, lower concentrations of the target analyte may be detected.

The methods and devices described herein may be used in conjunction with steady-state or thermal-wave analysis techniques. Various shapes of substrates may be used, and data (e.g., temperature) may be collected at various points, such as in the liquid to be analyzed, in a substrate coated with polymer material, or in a coated thermocouple.

Methods described herein may be used to provide real-time or nearly real-time characterization of bacteria that is conventionally performed in laboratories having complex equipment and highly trained personnel. Thus, the methods and devices may enable faster and cheaper data collection, and may enable improved outcomes by, for example, identifying bacterial outbreaks within a population. Such methods may be beneficial in health care, environmental and food safety (e.g., by detecting water-, air, and food-borne bacteria), and counter-terrorism (e.g., by detecting anthrax, etc.).

While the present disclosure has been described herein with respect to certain illustrated embodiments, those of ordinary skill in the art will recognize and appreciate that it is not so limited. Rather, many additions, deletions, and modifications to the illustrated embodiments may be made without departing from the scope of the disclosure as hereinafter claimed, including legal equivalents thereof. In addition, features from one embodiment may be combined with features of another embodiment while still being encompassed within the scope of the disclosure as contemplated by the inventors. Further, embodiments of the disclosure have utility with different and various detection devices and methods.

What is claimed is:

1. A method for characterizing bacteria, the method comprising:
    passing a buffer over and in contact with an imprinted polymer on a substrate;
    detecting a first temperature of the substrate;
    passing a liquid containing an analyte comprising a first bacteria and a second bacteria over and in contact with the imprinted polymer on the substrate, the imprinted polymer formulated to bind to the first bacteria, wherein a heat transfer property of the imprinted polymer varies based on an amount of the analyte bound thereto, and wherein the first bacteria binds to the imprinted polymer with a higher affinity than the second bacteria;
    binding a portion of the first bacteria and the second bacteria of the analyte to the imprinted polymer;
    removing at least a portion of the second bacteria from the imprinted polymer;
    detecting a second temperature of the substrate; and
    calculating a concentration of the first bacteria in the liquid based on the first temperature and the second temperature of the substrate.

2. The method of claim 1, wherein the first bacteria comprises living bacteria, and wherein the second bacteria comprises dead bacteria, the living bacteria and the dead bacteria being of the same species.

3. The method of claim 1, wherein the first bacteria comprises a first species, and wherein the second bacteria comprises a second species, the second species being an analogue of the first species.

4. The method of claim 1, wherein removing at least a portion of the second bacteria comprises washing the imprinted polymer.

5. The method of claim 4, wherein washing the imprinted polymer comprises rinsing the imprinted polymer with a phosphate buffered saline solution.

6. The method of claim 1, wherein passing a liquid containing the analyte over an imprinted polymer on a substrate comprises passing the liquid containing the analyte over an imprinted polymer selected from the group consisting of a molecularly imprinted polymer and a surface-imprinted polymer.

7. The method of claim 1, further comprising,
    detecting a temperature of the substrate before removing the at least a portion of the second bacteria from the imprinted polymer; and
    calculating a total concentration of the analyte in the liquid based on the temperature of the substrate before removing the at least a portion of the second bacteria from the imprinted polymer.

8. The method of claim 1, further comprising detecting a temperature of the liquid, wherein calculating a concentration of the first bacteria in the liquid is based on the temperature of the liquid.

9. The method of claim 1, further comprising providing a thermal wave from a heat transfer element through the imprinted polymer.

10. The method of claim 9, wherein calculating a concentration of the first bacteria in the liquid comprises calculating a concentration of the first bacteria in the liquid based on a phase shift between the thermal wave produced by the heat transfer element and an attenuated thermal wave having passed through the imprinted polymer.

11. The method of claim 9, further comprising generating the thermal wave with a controller configured to change a temperature of a temperature modification device thermally coupled to the heat transfer element.

12. The method of claim 9, wherein calculating a concentration of the first bacteria in the liquid comprises calculating a concentration of the first bacteria in the liquid based on a difference in amplitude between the thermal wave produced by the heat transfer element and the attenuated thermal wave having passed through the imprinted polymer.

13. The method of claim 9, wherein providing a thermal wave from a heat transfer element through the imprinted polymer comprises changing a frequency of the thermal wave.

14. The method of claim 9, wherein providing a thermal wave from a heat transfer element through the imprinted polymer comprises changing a temperature of the heat transfer element by less than 0.2° C.

15. The method according to claim 4, further comprising:
   passing the liquid over the imprinted polymer after washing the imprinted polymer; and
   washing the imprinted polymer at least a second time to remove the at least a second bacteria therefrom.

16. The method of claim 15, wherein washing the imprinted polymer comprises rinsing the imprinted polymer with a phosphate buffered saline solution.

17. The method of claim 15, wherein washing the imprinted polymer to remove the at least a second bacteria therefrom comprises removing the at least a second bacteria from the imprinted polymer without removing the first bacteria from the imprinted polymer.

18. The method of claim 15, wherein passing the liquid over the imprinted polymer after washing the imprinted polymer comprises increasing an amount of the first bacteria bound to the imprinted polymer.

19. The method of claim 6, wherein passing a liquid containing the analyte over an imprinted polymer on a substrate comprises passing the liquid containing the analyte over a molecularly imprinted polymer.

20. The method of claim 1, wherein removing at least a portion of the second bacteria from the imprinted polymer comprises removing unbound bacteria from the imprinted polymer.

\* \* \* \* \*

UNITED STATES PATENT AND TRADEMARK OFFICE
CERTIFICATE OF CORRECTION

PATENT NO. : 10,139,407 B2
APPLICATION NO. : 15/095636
DATED : November 27, 2018
INVENTOR(S) : Bart Robert Nicolaas Van Grinsven and Thomas Jan Cleij It is certified that error appears in the above-identified patent and that said Letters Patent is hereby corrected as shown below:

In the Specification
Column 9, Line 44, change "1.2±0.1 as" to --1.2±0.1 µm, as--
Column 11, Line 30, change "signal ($R_d$) increases" to --signal ($R_{th}$) increases--
Column 14, Line 22, change "*K pneumoniae*," to --*K. pneumoniae*,--

Signed and Sealed this
First Day of January, 2019

Andrei Iancu
*Director of the United States Patent and Trademark Office*